US008173837B1

(12) United States Patent
Fish

(10) Patent No.: US 8,173,837 B1
(45) Date of Patent: May 8, 2012

(54) PROCESS FOR THE PRODUCTION OF L-CITRULLINE FROM WATERMELON FLESH AND RIND

(75) Inventor: Wayne W. Fish, Bartlesville, OK (US)

(73) Assignee: The United States of America, as represented by the Secretary of Agriculure, Washington, DC (US)

( * ) Notice: Subject to any disclaimer, the term of this patent is extended or adjusted under 35 U.S.C. 154(b) by 315 days.

(21) Appl. No.: 12/630,294

(22) Filed: Dec. 3, 2009

(51) Int. Cl.
*C07C 227/00* (2006.01)
(52) U.S. Cl. ........................................ 562/514; 562/554
(58) Field of Classification Search .................. None
See application file for complete search history.

(56) References Cited

U.S. PATENT DOCUMENTS 1,539,161 A * 5/1925 Columbro ........................ 100/96
3,282,794 A * 11/1966 Okumura et al. .............. 435/114
4,956,471 A * 9/1990 Ito et al. ...................... 548/339.1

FOREIGN PATENT DOCUMENTS

CN 101372465 A * 2/2009
KR 2003000078 A * 1/2003

OTHER PUBLICATIONS

Rimando, Agnes et al., "Determination of citrulline in watermelon rind", Journal of Chromoatography A, 1078, 2005, 196-200.
Gornall, Allan Godfrey et al, XX. l-(+) Citrulline, The Department of Pathological Chemistry, University of Toronto.
Woo, Kang Lyung et al., "Capillary gas chromotographic determination of proteins . . . butyldimethylsilyl derivatives", Jnl of Chromot B, 665, 1995, 15-25.

* cited by examiner

*Primary Examiner* — Paul A Zucker
(74) *Attorney, Agent, or Firm* — John Fado; Randall E. Deck; Lesley Shaw

(57) ABSTRACT

L-citrulline may be extracted from watermelons using a process which does not require rigorous extraction with alcoholic and/or acidic solvents, or treatment at high temperatures. In the process, the watermelon juice is contacted with an adsorbent effective for adsorption of L-citrulline thereon, and the juice is separated therefrom. The L-citrulline on the adsorbent may then be eluted and recovered. Lycopene-containing microparticles may also be separated from the watermelon juice prior to contact with the adsorbent.

22 Claims, 3 Drawing Sheets

Citrulline Process Diagram

PROCESS FOR THE PRODUCTION OF L-CITRULLINE FROM WATERMELON FLESH AND RIND

BACKGROUND OF THE INVENTION

1. Field of the Invention

The invention relates to a novel process for recovering L-citrulline from watermelons.

2. Description of the Prior Art

In mammalian physiology, L-citrulline is a naturally occurring amino acid of the formula $H_2NC(O)NH(CH_2)_3CH(NH_2)CO_2H$ that functions in the detoxification of catabolic ammonia (urea production) and is a key element in the production of the vasodilator, nitric oxide. Moreover, arginine, the amino acid for which citrulline is an immediate precursor, is essential to several critical physiological functions such as immunostimulation and blood pressure control, in addition to its role as one of the 20 amino acids that make up proteins. However, almost all ingested free arginine is cleared by the liver and does not reach the bloodstream. In contrast, citrulline is not cleared from portal circulation and is converted to L-arginine in the kidney where it is then circulated to other organs in the body. Thus, significant attention has recently been given to the use of L-citrulline as an effective agent for arginine supplementation. Its potential therapeutic applications include short bowel syndrome, protein-energy malnutrition in aging, immunostimulation, and blood pressure control. These therapeutic uses are currently under clinical investigations (Curis et al. 2005. *Amino Acids.* 29:177-205).

Given its close metabolic relationship with L-arginine, L-citrulline can be found in at least small amounts in almost any living organism. In plants, citrulline is present at high levels in some Cucurbitaceae, especially the watermelon. Both the rind and flesh of watermelon contain citrulline at concentrations of 1-3 mg citrulline per g of fresh tissue (Rimando and Perkins-Veazie. 2005. *J. Chromatogr. A.* 1078: 196-200). Citrulline's role in watermelon is believed to be a protection against oxidative stress, especially during periods of drought.

Presently, citrulline is produced in China and Japan by fermentation of special strains of the microorganism, *Pseudomonas putida*. The recovery of L-citrulline from watermelon has been reported, but requires rigorous solution conditions for extraction, e.g., 6 M HCl at 145° C. for 4 hr (Woo and Lee. 1995. *J. Chromatogr. B* 665:15-19; Rimando and Perkins-Veazie. 2005. ibid). Thus, the need remains for an improved processes for the production of L-citrulline.

SUMMARY OF THE INVENTION

I have now invented a novel process for the production of L-citrulline from watermelon which does not require rigorous extraction with alcoholic and/or acidic solvents, or treatment at high temperatures. In the process of the invention, the watermelon juice is contacted with an adsorbent effective for adsorption of L-citrulline thereon. Following this contact, the treated juice is separated therefrom. The L-citrulline on the adsorbent may then be eluted and recovered. The process may be conducted using batch, semi-continuous or continuous systems. In a preferred embodiment, lycopene-containing microparticles are also separated from the watermelon juice prior to contact with the adsorbent.

In accordance with this discovery, it is an object of this invention to provide a method for preparing L-citrulline from watermelon.

Yet another object of this invention is to provide a method for preparing L-citrulline from watermelon without extraction with acid or alcohol solvents, or without exposure to elevated temperatures.

A further object of this invention is to provide a method which increases the availability of large quantities of L-citrulline from natural sources, such as watermelon.

Other objects and advantages of this invention will become readily apparent from the ensuing description.

DETAILED DESCRIPTION OF THE INVENTION

Watermelon contains large quantities of L-citrulline, with both the rind and the flesh containing concentrations of 1-3 mg citrulline per g of fresh tissue (Rimando and Perkins-Veazie. 2005. ibid). Whole watermelons are typically comprised of approximately 40% rind and 60% flesh, with the flesh being comprised of approximately 90% water and 10% solids (predominantly cells in a matrix of pectin and cellulose). The watermelons also contain large quantities of lycopene in this solid fraction, which is predominantly contained within subcellular microparticles or globular bodies (chromoplasts) enclosed by a phospholipid containing membrane.

Figure 1:
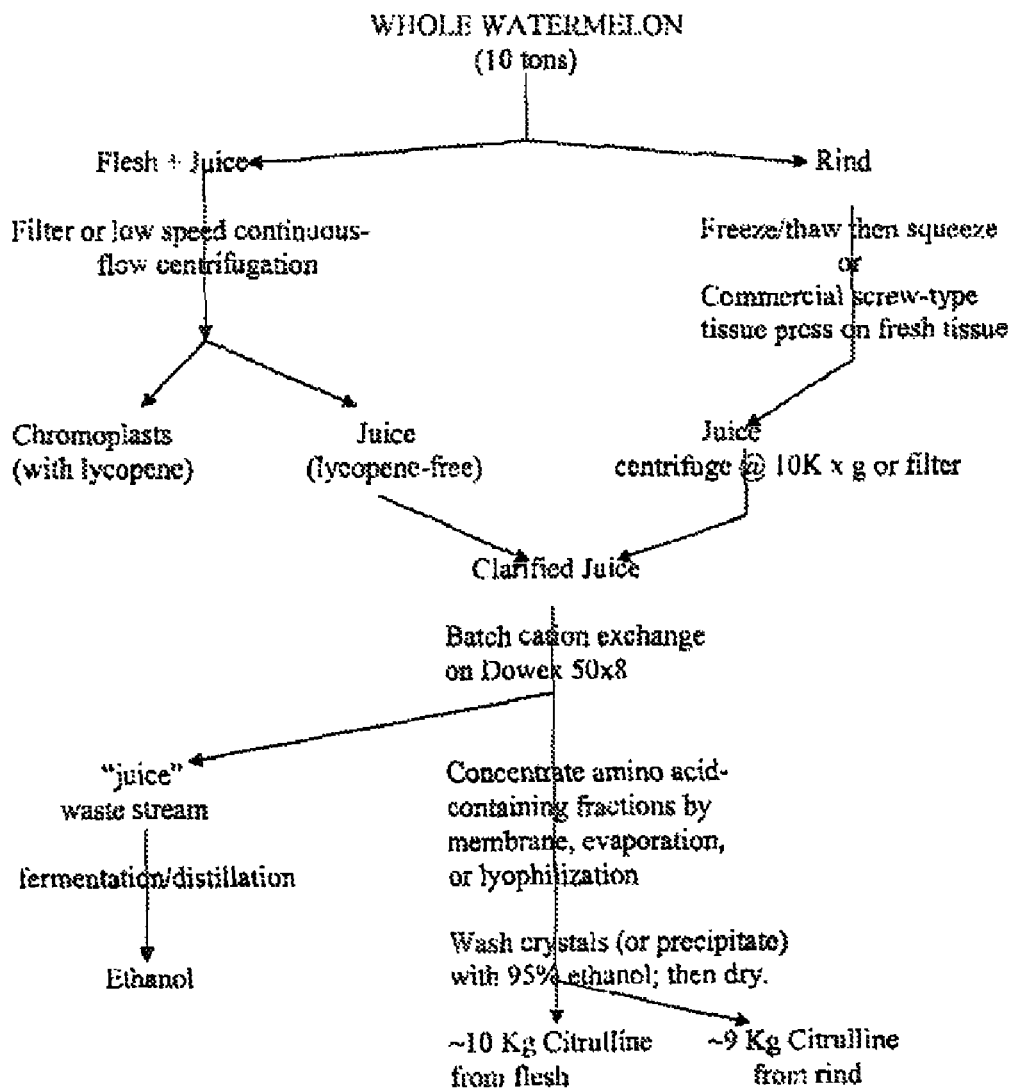
FIG. 1 is a flow diagram describing a preferred embodiment for the extraction of L-citrulline from watermelon.

Watermelon juice from which the citrulline is extracted may be derived from either the flesh or rind of the watermelon fruit. However, in accordance with the preferred embodiment as shown in FIG. 1, because citrulline is present in each, both the flesh and the rind are used as sources for the watermelon juice. In contrast with the prior art processes, this extraction of the citrulline from the watermelon fruit into the juice and the recovery of the resultant citrulline-containing juice, may be effected without the use or addition of an acid or an alcohol solvent (these steps are conducted in the absence of addition of significant quantities of acid or alcohol); neither the watermelon flesh nor the rind are treated with any significant quantities of acid or alcohol. Moreover, this extraction is conducted without the use of elevated temperatures, but rather is conducted at approximately ambient temperature.

To obtain the citrulline-containing juice from the flesh, the flesh of the fruit is treated to release the citrulline (as well as lycopene containing subcellular microparticles) from the cells into an aqueous suspension, and this citrulline and lycopene containing aqueous suspension is then separated from other insoluble solid phase materials, including cellular components such as fruit rind and intact cells, as well as non-membrane bound cell debris such as cell walls. Exclusive of subcellular lycopene-containing microparticles, the resultant citrulline-containing juice or crude extract is substantially free of these other insoluble solid phase materials, and typically contains less than about 15% thereof in the suspension, by weight. In one embodiment, this juice extracted from the fruit may be used as a starting aqueous suspension of the citrulline. Surprisingly, over 95% of the citrulline in the flesh is released into the juice in the process of this invention, without the use of the above-mentioned acid or alcohol solvents, or treatment at elevated temperatures. The juice may be extracted from the watermelon flesh using conventional techniques, including but not limited to, pressing the flesh, or by crushing or grinding followed by filtration, screening, centrifugation or settling, and recovering or retaining the liquid aqueous fraction (i.e., juice) which contains the citrulline therein.

The watermelon juice may be extracted from the rinds using conventional techniques, such as by grinding or pressing the rind, or both, and separating solids therefrom to yield the juice. In one embodiment, the rinds may be subjected to one or more freeze/thaw cycles, followed by application of pressure to squeeze the juice therefrom. Alternatively, in another embodiment, the rinds may be ground and pressed in a screw-type tissue press to extract the juice. The juice fraction collected from the rinds by either technique may be optionally, yet preferably, treated to separate and remove solid phase materials, such as by centrifugation (e.g. at 10,000×g), screening, settling or filtration, and recovering the liquid aqueous fraction or juice.

The resultant juice derived from the flesh and rind comprises an aqueous suspension of citrulline and lycopene containing subcellular microparticles. The watermelon juice may be optionally concentrated prior to extraction of the citrulline, although it is not required. Concentration may be effected using techniques conventional in the art, such as evaporation, reverse osmosis, membrane filtration or lyophilization.

As noted above, watermelon juice from the flesh of the fruit is also a rich source of lycopene, which is primarily contained within lycopene-containing subcellular microparticles. Thus, in an optional, yet preferred, embodiment, the watermelon juice recovered from flesh is further treated to separate and recover these lycopene-containing microparticles. Techniques for the separation and recovery of the lycopene-containing microparticles are described in applicant's copending U.S. patent application Ser. No. 11/387,312, filed Dec. 21, 2005, the contents of which are incorporated by reference herein. In brief, the lycopene-containing microparticles may be separated from the juice by settling, centrifugation and/or filtration. These microparticles may then be recovered and formulated as described in application Ser. No. 11/387,312. In a particularly preferred embodiment, the lycopene-containing microparticles are separated from the juice prior to the extraction of the L-citrulline as described hereinbelow. However, it is also envisioned that the lycopene-containing microparticles may be separated from the juice after the extraction of the L-citrulline.

Separation of the citrulline from the watermelon juice in accordance with the invention is effected by contacting the juice with an effective adsorbent for the citrulline. A variety of adsorbents are suitable for use herein, and include strong cation exchange adsorbents (resins) or strong anion exchange adsorbents (resins). Without being limited thereto, examples of strong cation exchange resins which may be used include sulfonated copolymers of styrene and divinylbenzene such as Dowex 50W or Dowex 50 (DOW Chemical Company, Midland, Mich.), while examples of strong anion exchange resins which may be used include quaternized amine derivatives of copolymers of styrene and divinylbenzene such as Dowex 1, Dowex 2, Dowex 11 or Dowex 21K. In addition, the strong anionic exchange resins may be in either their $OH^-$ or $Cl^-$ form, although anionic resins which are in their $OH^-$ form are preferred. Strong cation exchange adsorbents will allow negatively charged and uncharged molecules in the juice to pass through the resin bed while adsorbing or retaining the citrulline, other amino acids, and positively charged molecules thereon. On the other hand, strong anion exchange resins will adsorb or retain the citrulline, other amino acids, and negatively charged molecules thereon, while allowing passage of positive and uncharged molecules in the juice therethrough. It is also envisioned that two or more of the adsorbents may be used sequentially to afford more thorough purification of the citrulline. For example, following contact of the juice with one of a strong cation or anion exchange resin, the citrulline may be eluted therefrom and this eluate then contacted with the other of the strong cation or anion exchange resin. This sequential treatment with both the cationic and anionic exchange resins will effect the removal of substantially all charged and uncharged molecules (with the exception of other amino acids) from the citrulline.

Prior to application of the citrulline-containing juice onto the adsorbent, the pH of the juice should be adjusted according to the selected adsorbent. Thus, when using strong cation exchange resins, the juice is adjusted to an acidic pH, preferably to approximately 3-4, most preferably approximately 3, by addition of an acid thereto. Conversely, when using strong anion exchange resins, the juice is adjusted to an alkaline pH, preferably to approximately 8-12, most preferably approximately 10, by addition of a base thereto. Moreover, prior to the initial use of the adsorbents, as well as following completion of each cycle of elution of the citrulline from the adsorbent and its preparation for successive treatments, the skilled practitioner will recognize that the adsorbents should be regenerated in accordance with their manufacturer's recommendations. In brief, the strong cation exchange resins are typically regenerated by washing the resins in the contactor with an inorganic acid solution to convert the functional groups to their $H^+$ form, followed by a water rinse to a neutral pH. The strong anion exchange resins are typically regenerated by washing the resins in the contactor with a basic solution such as NaOH or NaCl to convert the functional groups to their $OH^-$ or $Cl^-$ forms, respectively, followed by a water rinse to a neutral pH.

Contact of the watermelon juice with the adsorbent may be effected using any conventional solid/liquid contactors, including but not limited to packed bed columns or chromatography columns, stirred tanks, fluidized beds or simulated moving beds. The operation may be conducted as a batch, semi-continuous or continuous system. For example, in one embodiment, the watermelon juice may be contacted with the adsorbent by directing the flow of the juice substantially upwardly through the adsorbent, such as in an anti-gravity column. Directing the flow upward in this fashion limits the pressure drop caused by any undissolved solids in the juice. In another embodiment, the process may utilize multiple columns for treatment of the juice with the adsorbent. Temperature, for the citrulline adsorption is not critical. Although temperatures of about 10° C. to about 60° C. are suitable for use herein, contacting at ambient temperature is generally preferred. The relative amounts of the adsorbent and juice will vary with the particular adsorbent and contactor system, and may be readily determined by routine experimentation. However, by way of illustration and without being limited thereto, in batch, packed bed column systems, approximately 1 liter bed volumes of the above-mentioned Dowex resins are effective for treatment of 10 liters of watermelon juice.

Figure 2:
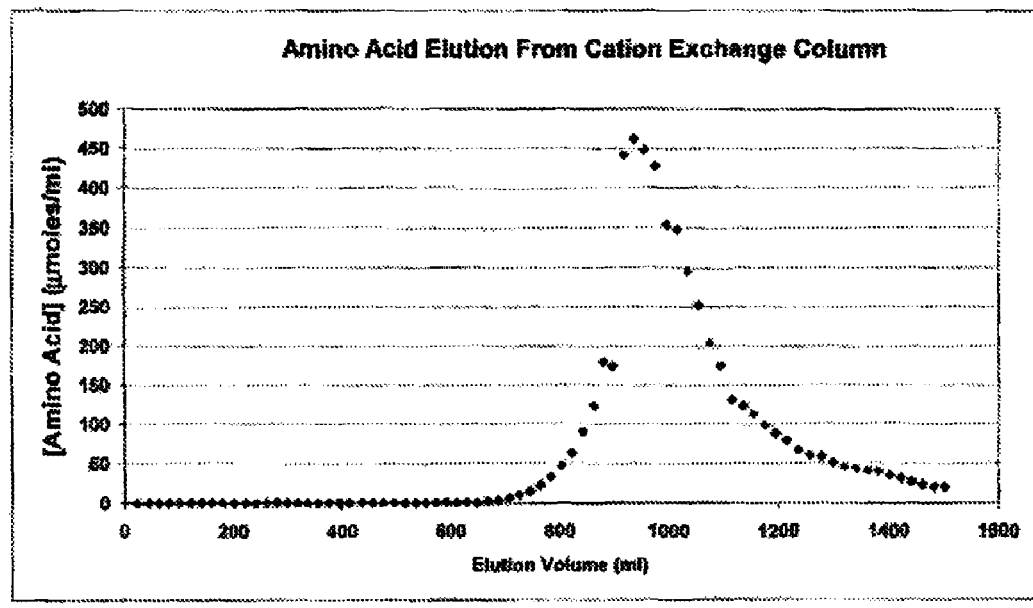
FIG. 2 shows the results of L-citrulline prepared from watermelons using cation exchange chromatography to isolate the L-citrulline and other amino acids as described in Example 1.

Following the adsorption of the citrulline on the ion exchange media, the remaining voided juice (which may also be referred to as the permeate or filtrate) is separated. The voided juice, which is substantially citrulline-free, may be discarded or recovered for subsequent use as described hereinbelow. In an optional yet preferred embodiment, after separation of the voided juice and before elution of the citrulline, the adsorbent is washed to remove unbound material. Aqueous acidic solutions, pH approximately 3, are preferred for washing the cation exchange resins, while aqueous alkaline solutions, pH approximately 10, are preferred for washing the anion exchange resins. The citrulline may then be recovered by elution from the adsorbent using appropriate eluant. Suitable eluants for use with strong cation exchange resins are bases which are effective to titrate the active groups on the resin and raise the pH, thus releasing the bound citrulline and amino acids into solution. A typical elution profile from a cation exchange column is shown in FIG. 2. Thus, typical eluants for use with strong cation exchange resins include, but not limited to, 1M $NH_4OH$, NaOH or KOH. On the other hand, suitable eluants for use with strong anion exchange resins are acids which are effective to titrate the active groups on the resin and lower the pH, thereby releasing the bound citrulline and amino acids into solution. Typical eluants for use with strong anion exchange resins include, but not limited to, 1M $H_2SO_4$, HCL or $HNO_3$. The pH of the citrulline-containing eluant or fraction which is recovered is preferably adjusted to approximately between 5 and 6. The used adsorbents may be regenerated as described above. The eluate may be monitored for amino acids by use of a reagent that reacts with amino groups such as ninhydrin. An alternative, faster method, although not as accurate as ninhydrin, is to monitor the pH of the eluate. Amino acids will elute just ahead of and behind the leading edge of the eluate pH change. Eluate is collected after ~1.5 column volumes through 3 column volumes (pH starts to rise at 1.5 column volumes and pH rises to >13) if monitoring pH change to collect the L-citrulline. Monitoring of eluate from an anion exchange column follows the same procedure except the pH of the eluate drops to below pH 1.

The citrulline-containing eluant comprises substantially pure citrulline and other amino acids and may be recovered directly for subsequent use or it may be optionally concentrated and/or further purified. For example, as shown in FIG. 1, in the preferred embodiment the citrulline-containing eluate is concentrated to remove water therefrom and produce a concentrated L-citrulline liquid- or solid-phase composition. A variety of techniques are suitable for concentrating the citrulline, and include, but are not limited to, evaporation (including spray or drum drying), reverse osmosis, membrane filtration (e.g., nanofiltration) or lyophilization. The concentrated citrulline may also be washed with alcohol such as ethanol, or crystallized following treatment with a water/alcohol mixture. Citrulline is the predominant amino acid in the concentrated product, and the citrulline content of a typical dried citrulline product prepared as described in this process may be over 80%, by weight.

Yields of L-citrulline prepared using the process of this invention may vary somewhat with the particular adsorbent selected, but are typically approximately 19 Kg citrulline per 10 tons of whole watermelons. Of this amount, approximately 10 kg is derived from the watermelon flesh and the remaining 9 Kg is derived from the rind. Thus, over 95% of the citrulline in the flesh of watermelon is recovered. These high yields are surprisingly obtained without the use or addition of an acid or an alcohol solvent for extracting the citrulline from the watermelon fruit into the juice and recovering the resultant citrulline-containing juice.

The citrulline formulations prepared in accordance with this invention are suitable for use in the neutraceutical industry and in a variety of clinical applications requiring arginine supplementation.

In addition to the providing the primary citrulline product, the voided juice by-product separated from the adsorbent may also be retained for subsequent use. In accordance with a preferred embodiment, the voided juice is recovered and fermented with an ethanologenic microorganism effective to produce ethanol. A variety of microorganisms and fermentation processes have been described for the fermentation of hexose and/or pentose compositions derived from agricultural commodities and are suitable for use herein. In brief, the voided juice is contacted with an appropriate microorganism under conditions effective for the fermentation of the sugars therein to ethanol. Although numerous microorganisms have been described for ethanol fermentations, use of *Saccharomyces cerevisiae* is preferred.

The following example is intended only to further illustrate the invention and is not intended to limit the scope of the invention which is defined by the claims.

Example 1

Citrulline was prepared from whole watermelons produced in Oklahoma using the same process shown in FIG. 1 with the exception of the amount of watermelon treated. Watermelon juice was prepared from watermelon flesh or rind by grinding and/or pressing. The liquid was separated from residual solids by settling then filtration and/or centrifugation. Lycopene-containing chromoplasts were removed from the juice of watermelon flesh by settling at pH 3 or by centrifugation @ 2,000×g for 15 min.

Citrulline separation was effected using a five hundred ml bed of Dowex 50Wx8-400 cation exchange resin. (Dow Chemical Company, Midland, Mich.). The resin in the column was washed with 2% $H_2SO_4$ then water to convert the functional groups to the $H^+$ form. The pH of the watermelon juice extract was adjusted to pH 3 before application to the column. Five liters of chromoplast-free, pH adjusted watermelon juice was applied to the cation exchange resin bed. After sample application and separation of the voided watermelon juice, column containing the adsorbed citrulline was washed with 1 liter of water, pH 3. The citrulline was then eluted with 1 M KOH, and twenty ml fractions were collected. The pH was measured in individual fractions followed by quantification of amino acids by reaction with ninhydrin (Rosen. 1957. A modified ninhydrin calorimetric analysis for amino acids. *Arch. Biochem. Biophys.* 67:378-383). Fractions between 800 ml and 1300 ml were pooled and concentrated. The elution profile is shown in FIG. 2.

Figure 3:
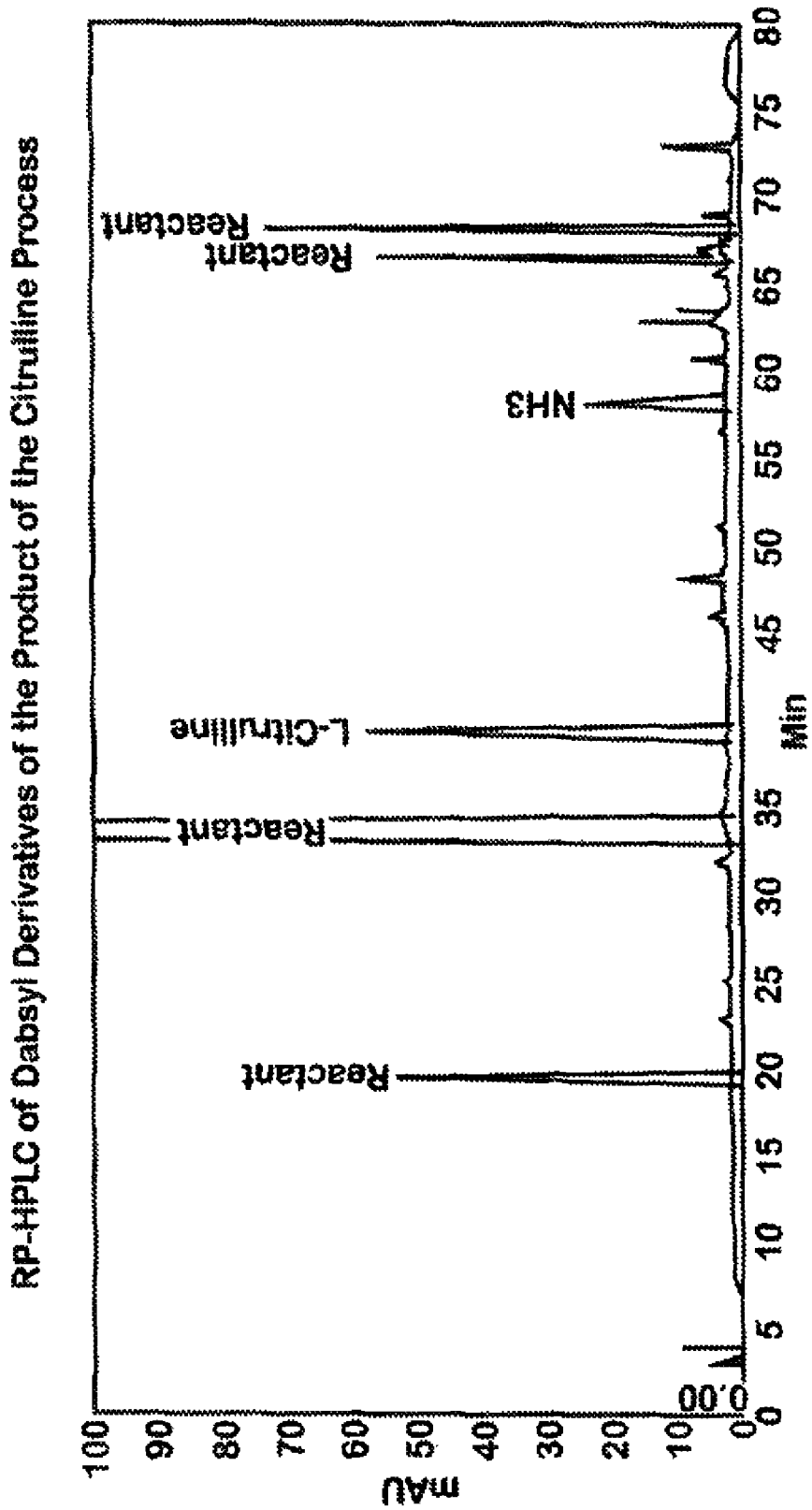
FIG. 3 shows the HPLC analysis of watermelon citrulline prepared by the process described in the example.

The content of L-citrulline in the preparation was determined by reversed phase HPLC separation and quantification of the DABSYL derivatives of the amino acids as shown in FIG. 3. Samples were derivatized with DABSYL chloride and subjected to reversed phase HPLC on a C-18 column according to the procedure of Sethuraman et al. (2004. Simple quantitative HPLC method for measuring physiologic amino acids in cerebrospinal fluid without pretreatment. *Clinical Chem.* 50:665-669). The L-citrulline content of a typical sample prepared by the process described herein is 86+5%.

It is understood that the foregoing detailed description is given merely by way of illustration and that modifications and variations may be made therein without departing from the spirit and scope of the invention.

I claim:

1. A process for preparing L-citrulline from watermelon comprising:
   a. providing watermelon juice comprising L-citrulline,
   b. contacting said juice with an adsorbent effective for adsorption of L-citrulline thereon,
   c. separating the voided juice from said adsorbent, and
   d. recovering the L-citrulline from said adsorbent.

2. The process of claim 1 further comprising concentrating said L-citrulline recovered from said adsorbent to remove water therefrom.

3. The process of claim 2 wherein said concentrating comprises evaporation, reverse osmosis, membrane filtration or lyophilization of said L-citrulline-containing fraction.

4. The process of claim 2 further comprising washing said L-citrulline following said concentrating.

5. The process of claim 1 wherein said adsorbent is selected from the group consisting of a strong cation exchange resin and a strong anion exchange resin.

6. The process of claim 1 wherein said watermelon juice comprising said L-citrulline is prepared from the flesh, rind or both of said watermelon.

7. The process of claim 6 wherein said watermelon juice comprising said L-citrulline is prepared from both the flesh and the rind of said watermelon.

8. The process of claim 6 wherein said watermelon juice comprising said L-citrulline is prepared from said flesh by grinding watermelon flesh and separating solids therefrom.

9. The process of claim 6 wherein said watermelon juice comprising said L-citrulline is prepared from said rind by grinding or pressing said rind, or both, and separating solids therefrom.

10. The process of claim 6 wherein said watermelon juice comprising said L-citrulline is not extracted from said flesh with use of an acid or an alcohol solvent.

11. The process of claim 1 which is conducted at approximately ambient temperature.

12. The process of claim 10 which is conducted at approximately ambient temperature.

13. The process of claim 1 wherein said watermelon juice further comprises lycopene-containing microparticles, and said process further comprises separating said lycopene-containing microparticles from said juice.

14. The process of claim 13 further comprising recovering said lycopene-containing microparticles.

15. The process of claim 13 wherein said separating said lycopene-containing microparticles from said juice is prior to said contacting.

16. The process of claim 1 further comprising retrieving said voided juice separated from said adsorbent.

17. The process of claim 16 further comprising fermenting said voided juice separated from said adsorbent with an ethanologenic microorganism effective to produce ethanol.

18. A process for preparing L-citrulline from watermelon comprising:
    a. providing watermelon juice comprising L-citrulline and lycopene-containing microparticles,
    b. separating said lycopene-containing microparticles from said juice to produce a clarified juice,
    c. contacting said clarified juice with an adsorbent effective for adsorption of L-citrulline thereon,
    d. separating the voided juice from said adsorbent, and
    e. recovering the L-citrulline from said adsorbent.

19. The process of claim 18 wherein said watermelon juice comprising said L-citrulline is prepared from the flesh, rind or both of said watermelon.

20. The process of claim 19 wherein said watermelon juice comprising said L-citrulline is not extracted from said flesh with an acid or an alcohol solvent.

21. The process of claim 18 which is conducted at approximately ambient temperature.

22. The process of claim 20 which is conducted at approximately ambient temperature.

* * * * *